US00PP18371P3

(12) United States Plant Patent
Saville

(10) Patent No.: US PP18,371 P3
(45) Date of Patent: Dec. 25, 2007

(54) ***HOSTA* PLANT NAMED 'BECKONING'**

(50) Latin Name: *Hosta hybrid (Tratt.)*
Varietal Denomination: Beckoning

(76) Inventor: Timothy Saville, 12 Burnham Close, Cheadle Hulme, Cheshire (GB), SK8 6DN ( * ) Notice: Subject to any disclaimer, the term of this patent is extended or adjusted under 35 U.S.C. 154(b) by 0 days.

(21) Appl. No.: 11/388,059

(22) Filed: Mar. 23, 2006

(65) Prior Publication Data

US 2007/0226861 P1 Sep. 27, 2007

(51) Int. Cl.
*A01H 5/00* (2006.01)

(52) U.S. Cl. ..... Plt./353

(58) Field of Classification Search ..... Plt./353
See application file for complete search history.

*Primary Examiner*—Kent Bell
*Assistant Examiner*—June Hwu

(57) ABSTRACT

A new and distinct *Hosta* plant named 'Beckoning' characterized by heat-shaped, large-sized, leaves with blue-green margins, yellowish leaf centers, tall vertical flower scapes with many near white flowers held nicely above foliage, suitable for landscape, potted culture, or cut flower arrangements.

2 Drawing Sheets

Botanical classification: *Hosta* hybrid (Tratt.).
Variety denomination: 'Beckoning'.

SUMMARY, BACKGROUND AND ORIGIN OF THE PLANT

The new and distinct *Hosta* plant, hereinafter also referred to as 'Beckoning' and "the plant" is a new and distinct cultivar of hosta. It was found by Timothy Saville in 1998 as an un-induced whole plant sport of the *Hosta* cultivar 'Blue Angel' (not patented) in a now defunct nursery in Cheshire, England. The plant has been successfully propagated by division and tissue culture methods at a perennial plant nursery in Zeeland, Mich. and found to produce identical plants that maintain the unique characteristics of the original plant. The plant is stable and reproduces true to type in successive generations of asexual reproduction.

*Hosta* 'Beckoning' differs from its parent sport, 'Blue Angel', all other known sports of 'Blue Angel' as well as all other hostas known to the applicant, in that the plant is variegated with a lutescent gold center emerging in the spring as nearly solid colored and gradually developing the yellow center with warmer temperatures. *Hosta* 'Blue Angel' also has some other sports including: 'Earth Angel' (not patented), 'Guardian Angel' (not patented), and 'Fallen Angel' (not patented). 'Beckoning' has a blue-green margin with a gold center of each leaf. *Hosta* 'Guardian Angel' has a blue green margin but the center is a misted whitish-green that tends to become all green in the heat of the summer. 'Fallen Angel' has the same whitish-green misting as 'Guardian Angel' through the entire leaf and does not have the solid blue-green margin. 'Earth Angel' has a creamy-yellow margin that is lighter than the center of 'Beckoning', and has the same blue-green in the center that 'Beckoning' has on the margin. The most similar known hosta cultivars in color are 'June' (not patented) and 'Paul's Glory' (not patented). 'June' grown in the shade has a similar color pattern as 'Beckoning' grown in the sun, but the new plant is between two and three times the size of 'June' in habit, clump height and width as well as leaf size. *Hosta* 'Paul's Glory' is slightly smaller in size of leaf and clump dimensions, and similar in colors, but the margin is less distinct, or more defused between the margin and center of the leaf on 'Paul's Glory' and more distinctly featured or jetting on 'Beckoning'.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
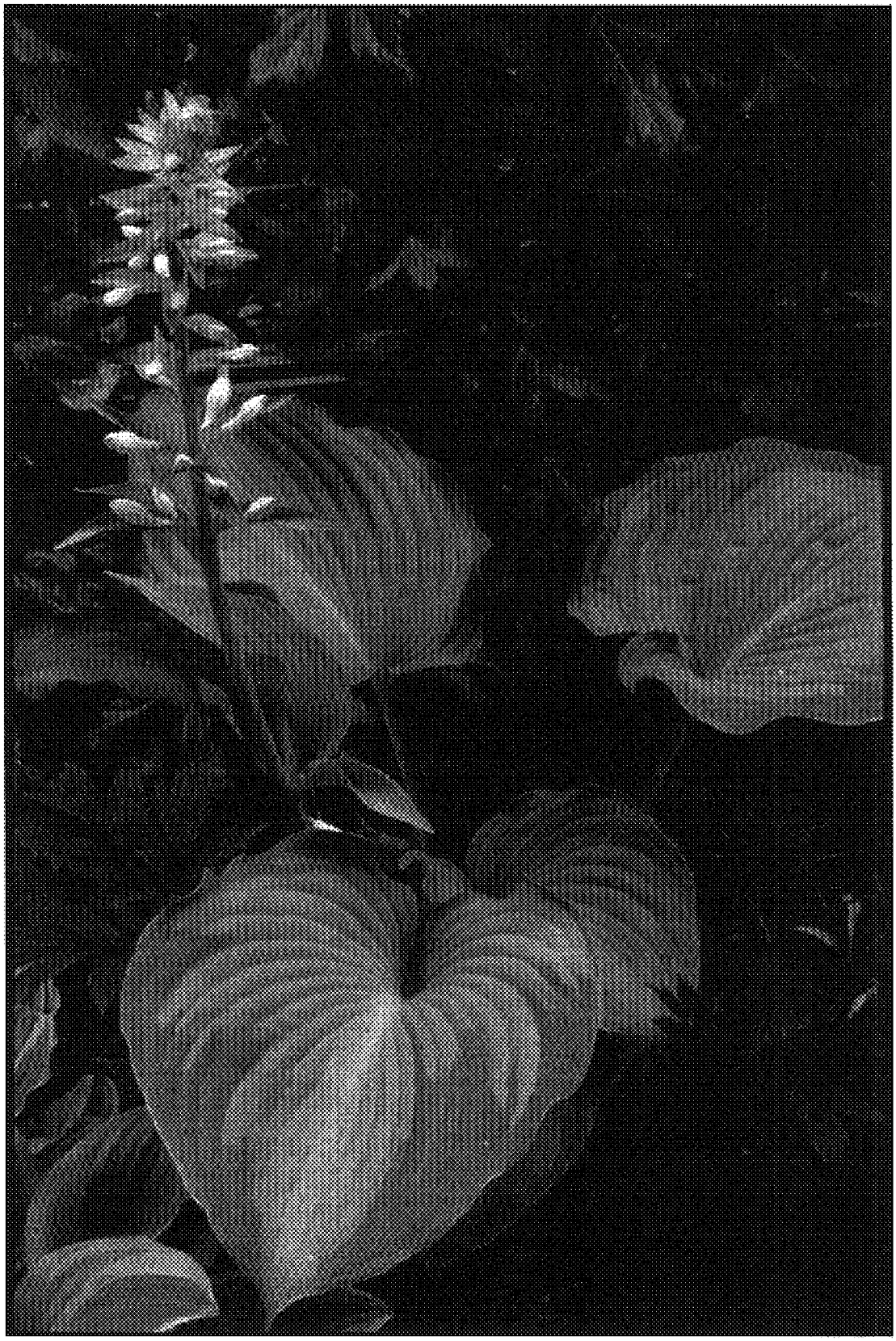
FIG. 1 shows the overall plant at the beginning of flowering.
Figure 2:
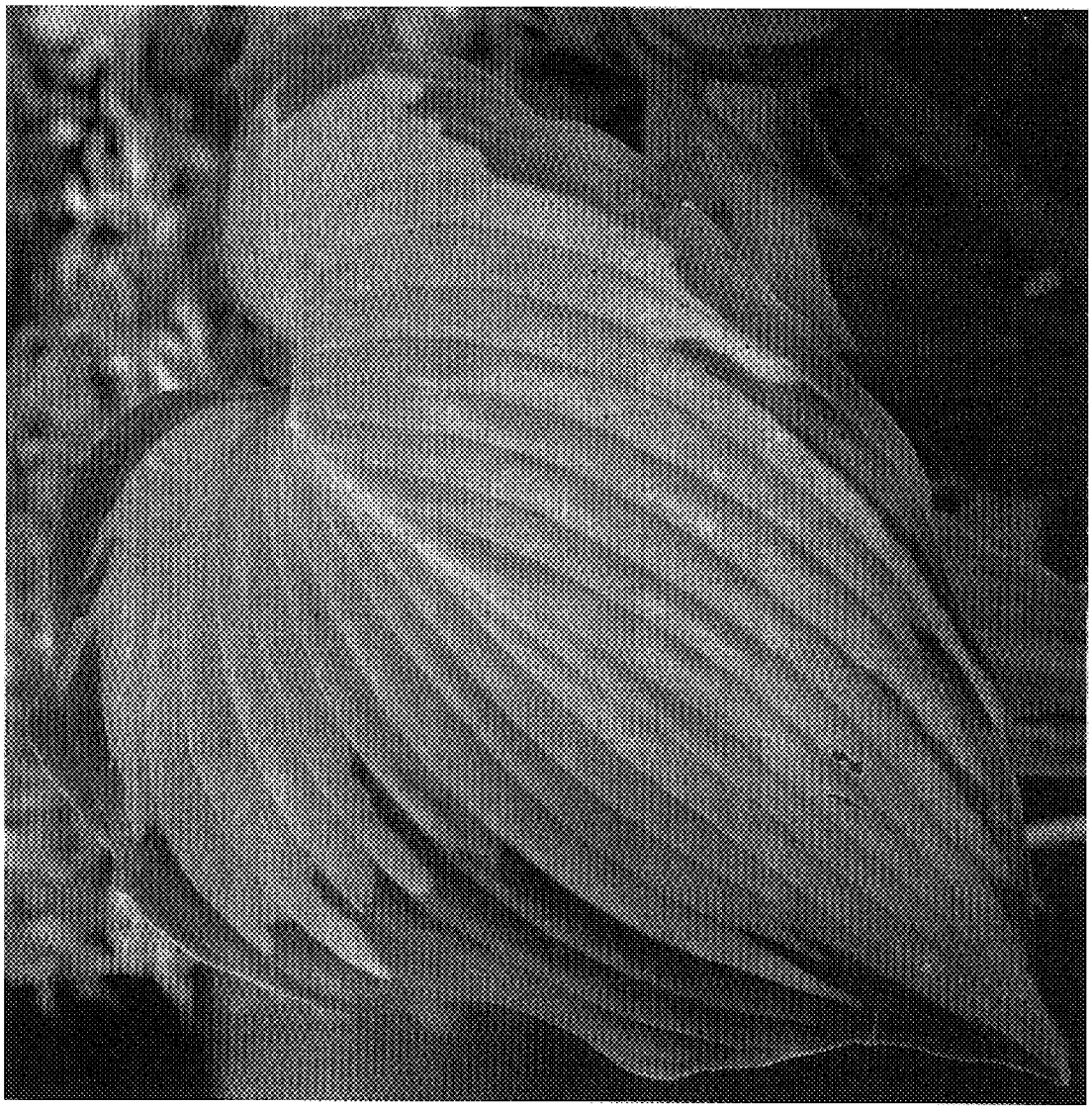
FIG. 2 shows the leaf later in the season.

The genus *Hosta* is mainly native to Japan with a few species originating from China and Korea. There are over 3,300 cultivars registered with The American Hosta Society, which is the International Cultivar Registration Authority for the genus *Hosta*. *Hosta* 'Beckoning' differs from all of these in that it has:

1. Rugose pointed heart-shaped leaves with blue-green margins and gold centers
2. Large plant size in clump habit and leaf dimensions
3. Tall scapes with many light lavender flowers.

DETAILED BOTANICAL DESCRIPTION

The following descriptions and color references are based on the 2001 edition of The Royal Horticultural Society Colour Chart except where common dictionary terms are used. The new plant, *Hosta* 'Beckoning', has not been observed under all possible environments. The phenotype may vary slightly with different environmental conditions, such as temperature, light, fertility, moisture and maturity levels, but without any change in the genotype. The following observations and size descriptions are of a four-year old plant in a garden in Stockport, Cheshire, United Kingdom.

Botanical classification: *Hosta*×hybrid.

Parentage: naturally occurring sport of *Hosta* 'Blue Angel' (not patented).

Propagation:

*Method.*—By tissue culture and division.

*Time to initiate roots from both division and tissue culture.*—Two to three weeks.

*Rooting habit.*—Normal, fleshy, lightly branching.

Plant description:

*Plant shape and habit.*—Hardy herbaceous perennial with basal rosette leaves, symmetrical and arching over.

*Crop time.*—Under normal growing conditions about 18 weeks to finish in a one-liter container. Plant vigor is good to high.

*Plant size.*—Foliage height at flowering is 45 to 55 cm tall from soil line to the top of the leaves and 50 to 60 cm wide.

Foliage description:

*Shape and size.*—Cordate leaf blades have an acute apex and auriculate base. The leaf blades are 30 to 35 cm long and 25 to 30 cm wide. The leaf blade margin is entire and the variegation pattern on the edge varies in different regions of the leaf from 10 to 25 mm wide. The leaves have between 16 and 18 pairs of major parallel veins.

*Blade color.*—Young emerging leaves. Top surface margin and center: RHS 137C; Underside margin and center: RHS 191 B.

*Top surface of mature leaves while still containing glaucous wax.*—Top surface margin: RHS 119A and RHS 116 D. Top surface center: more yellow than RHS 144B. Underside margin: more blue than RHS 189A, and more gray than RHS N138A. Underside center: between RHS 147D and RHS 148D.

*Mature leaves later in the growing season.*—Top center: RHS 160B. Top margin: between RHS 137A and RHS 139A. Bottom surface margin: RHS 189A on the margin before the glaucous wax diminishes and RHS 137A once the wax is gone. Bottom surface centers: between RHS 147C and RHS 147D before the wax is lost, and RHS 160B after loss of the glaucous wax.

There are two or three intermediate and inconsistent color patterns between the center and the margin. The most prominent intermediate color bands on the top surface are RHS 136 C and RHS 133 C.

*Veins.*—The 16 to 18 prominent veins pairs, while depressed on the top surface and slightly protruding on the bottom, are the same color as the surrounding leaf tissue in all observed conditions.

*Petioles.*—30 to 45 cm long and 1.5 to 2.0 cm wide. The leaf margin continues on the petiole 1 to 2 mm wide and RHS N138 C on both sides, and the center is RHS 144 B on the inside and RHS 144A on the outside.

Flower description:

*Buds.*—One day prior to opening lighter than RHS 97 D; 4.5 to 5.5 cm long, up to 1.5 cm wide; clavate with broadly acute apex and longer thin base.

*Flowers.*—50 to 70 per scape; funnelform; 4 to 6 cm wide and 6 to 8 cm long, (distal flowers being smaller), persists for a normal period, up to two days on or cut from plant, and the scapes remain effective from early July to mid August; No detectable fragrance.

*Tepal.*—Two sets of three fused at the base; clavate with acute apex; entire; approximately 5 cm long and 1.2 cm wide; inner set of three tepals with 1 to 2 mm clear margin; outer surface RHS 85D with veins RHS 85C, inside surface between RHS 85A and RHS 85B in the center and whiter than RHS 85D in the margin 3 mm.

*Gynoecium.*—Single; Style — 7 to 8 cm long, white, lighter than RHS 155D, 1 mm diameter, curled at distal end;

*Stigma.*—2 mm to 3 mm in a diameter, white, lighter than RHS 155D;

*Androecium.*—Filaments — six, white, approximately 1 mm in diameter and to 5 cm long, lighter than RHS 155D;

*Anthers.*—5 to 6 mm long, 1.5 mm wide; closest to RHS N92A;

*Pollen.*—Abundant, RHS 14A;

*Fruit.*—Dehiscent three chambered loculicidal capsule; 3.0 to 3.5 cm long and 6 mm wide, between RHS 138A and RHS 138B;

*Seeds.*—Flattened, single-winded dried; about 3 mm wide and 6 mm long, RHS 200A, about 30 per fruit;

*Bract.*—Sessile with acute apex, protruding from scape at near right angle; up to 7 cm long and 1.5 cm wide, progressively smaller near distal end of scape, RHS 139 C in the top and bottom surfaces in the center and sometimes with a thin 1 to 2 mm wide margin of RHS 137 B on both surfaces.

*Peduncle.*—Generally unbranched raceme, one per mature division; erect 95 to 110 cm tall and to 1 cm diameter, average height 100 cm, average width 1 cm, light green color RHS N138 B with a glaucous surface.

*Pedicel.*—Approximately 1.05 to 1.5 cm long, 3 mm wide, RHS N138 C to RHS N138 D.

Disease resistance: Resistance beyond that of other hostas has not been observed. The plant grows best with plenty of moisture and adequate drainage, but is able to tolerate some drought when mature. Hardiness at least from USDA zone 3 through 9, and other disease resistance is typical of that of other hostas.

I claim:

1. A new and distinct cultivar of ornamental *Hosta* plant named 'Beckoning' as herein described and illustrated, with yellowish leaf center and blue-green margin, suitable as a potted plant, for the garden, and for cut flower arrangements.

* * * * *